United States Patent [19]

Berkhoff et al.

[11] Patent Number: 4,775,621

[45] Date of Patent: Oct. 4, 1988

[54] METHOD OF DISTINGUISHING INVASIVE E. COLI THAT CAUSE SEPTICEMIA

[75] Inventors: Herman A. Berkhoff; Andrew C. Vinal, both of Raleigh, N.C.

[73] Assignee: North Carolina State University, Raleigh, N.C.

[21] Appl. No.: 833,881

[22] Filed: Feb. 25, 1986

[51] Int. Cl.$^4$ .............................................. C12Q 1/10
[52] U.S. Cl. ...................................... 435/38; 432/29; 432/34
[58] Field of Search ............................. 435/29, 38, 34

[56] References Cited

PUBLICATIONS

Shelley M. Payne and Richard A. Finkelstein, *Infection and Immunity 18,* 94 (1977).
E. K. Barbour, N. H. Nabbut and H. M. Al-Nakhli, *Am. J. Vet. Res. 46,* 989 (1985).
Panagiotis A. Daskaleros and Shelley M. Payne, *Infection and Immunity 48,* 165 (1985).
Anthony T. Maurelli, Barbara Blackmon and Roy Curtiss, III, *Infection and Immunity 43,* 397 (1984).
Edward E. Ishiguro, Teresa Ainsworth, Trevor J. Trust and William W. Kay, *J. Bacteriol. 164,* 1233 (1985).
Michael J. Surgalla and Earl D. Beesley, *Applied Microbiology 18,* 834 (1969).
J. Kaya Prpic, Roy M. Robins-Browne and R. Brent Davey, *Journal of Clinical Microbiology 18,* 486 (1983).
John J. Johnson and W. S. Chilton, *Science 152,* 1247 (1966).

*Primary Examiner*—Sam Rosen
*Attorney, Agent, or Firm*—Bell, Seltzer, Park & Gibson

[57] ABSTRACT

A method for distinguishing invasive from noninvasive *E. coli* comprises collecting an undifferentiated bacterial sample from a host, contacting bacteria contained in the sample to a growth medium which contains a dye selectively taken up by invasive *E. coli*, incubating the growth medium to grow colonies of *E. coli*, and examining the growth medium to detect *E. coli* colonies which have taken up the dye. A two-step incubation procedure provides superior results. While the invention can be practiced with *E. coli* obtained from any host, specific procedures for practicing the invention in poultry are provided.

34 Claims, No Drawings

METHOD OF DISTINGUISHING INVASIVE *E. COLI* THAT CAUSE SEPTICEMIA

TECHNICAL FIELD

This invention generally relates to the diagnosis of disease, and particularly relates to the diagnosis of diseases caused by invasive *Escherichia coli* bacteria with dyes which are selectively taken up by invasive strains of *Escherichia coli*.

BACKGROUND OF THE INVENTION

*Escherichia coli* (*E. coli*) bacteria are ordinarily harmless bacteria found as part of the natural microbial flora in a number of animals. In humans, *E. coli* form a major part of the natural flora of the large intestine. Some types of *E. coli*, however, have the capacity to invade the tissue of their host, resulting in severe, and ofttimes fatal, disease.

In poultry, invasive *E. coli* cause colisepticemia: the disease that results in the greatest loss to poultry producers in the United States and worldwide of all poultry diseases. In calves and pigs, neonatal colisepticemia is a major cause of mortality, and in humans—particularly among infants in third-world countries—*E. coli* can invade the blood and the membranes which envelope the brain and spinal cord to produce neonatal meningitis.

There has not heretofore been available a simple, reliable test for distinguishing invasive, disease-causing *E. coli* from harmless, noninvasive *E. coli* in an undifferentiated bacterial sample taken form a host organism (a sample which contains a number of distinct types of bacteria). Such a test would, however, have a profound impact on the prevention and control of septicemic *E. coli* infections in animals and humans.

Previously, such diseases were diagnosed by isolating *E. coli* from tissue which would normally be free of bacteria (such as the liver and brain) after the tissue had been invaded, or by the use of serotyping. Serotyping, a widely used procedure by which bacteria are classified according to the kinds and combinations of antigens found on each strain of bacteria, has proven to be unreliable for this particular purpose.

Payne and Finkelstein, Infection and Immunity, 18, 94 (1977) found that colonies of a previously isolated and established strain of virulent *E. coli* bacteria were stained when raised on a growth media containing Congo Red dye, while nonvirulent variants of that strain were not stained by the dye. They suggest that their procedure could be useful for selecting the few harmless mutants which can be found in a previously isolated strain of virulent bacteria so that the harmless mutants could be used in vaccines. No suggestion is made that the procedure would be useful for detecting the few invasive *E. coli* in an undifferentiated bacterial sample taken from a host organism—a sample which would be largely comprised of harmless strains of *E. coli*.

The manner by which colisepticemia is transmitted in poultry has not been well understood. It has generally been believed to arise as a secondary infection following a primary infection by a virus, mycoplasma, or other virulent microbe. Barbour, Nabbut and Al-Nakhli, *Am. J. Vet. Res.*, 46, 989 (1985), who investigated the source of *E. coli* infections in poultry by collecting bacterial samples from hearts and livers of dead and moribund birds, generally suggest the breeding farm as the main source of the problem, but they used serotyping to distinguish invasive from noninvasive *E. coli*—a procedure which does not produce reliable results for this purpose. No suggestion is made as to how colisepticemia could be predicted in a poultry flock without the use of serotyping, and without the use of bacteria obtained from tissue samples.

DESCRIPTION OF THE INVENTION

Applicants herein disclose a simple, reliable method for distinguishing, in an undifferentiated bacterial sample, those *E. coli* bacteria which are capable of invading the tissue of a host from those *E. coli* which cannot. This method begins with the collection of an undifferentiated bacterial sample containing *E. coli* from a host organism, such as a chicken, turkey, calf, pig or human. Bacteria from this sample are then contacted to a growth medium, which growth medium contains a dye which is selectively taken up by invasive *E. coli* bacteria, so that the growth medium is inoculated with *E. coli* bacteria. The growth medium is then incubated for a time, and at a temperature, sufficient to grow colonies of *E. coli*. Following incubation, the growth medium is inspected to detect the presence or absence of *E. coli* colonies which have taken up the dye. The presence of such colonies indicates the presence of invasive *E. coli* bacteria in the host. Thus, applicants have provided a procedure in which invasive *E. coli*, in an undifferentiated bacterial sample taken from a host organism, are distinguished from harmless *E. coli* through the use of a selective dye. Specific details of how this method is practiced are provided below.

The present invention can be practiced with bacterial samples obtained from a variety of hosts, including swine, cattle and humans. In poultry, we have found that the procedure can be used to predict in advance whether a paraticular flock of birds will be afflicted with colispeticemia.

Whether or not colisepticemia will occur in the offspring of a poultry breeder flock can be determined by, first, collecting undifferentiated bacterial samples containing *E. coli* from the cloacas of selected birds in the breeder flock. The samples are collected by taking cloacal swabs from both hens and toms. Swabs should be taken from a sufficient number of birds to ensure an adequate sampling of the flock, preferably at least 2% of the birds in the flock. These bacteria are then contacted to a growth medium and incubated according to the same procedure as described above. The presence of colonies of *E. coli* on the growth medium which have taken up the dye indicates that the offspring of the breeder flock will be afflicted with colisepticemia and airsacculitis (airsacculitis being one particular lesion, in the bird respiratory system, produced by colisepticemia).

We have also found that the occurrence of colisepticemia in poultry can be predicted by exposing a growth medium containing a dye which is selectively taken up by invasive *E. coli* to the atmosphere within a poultry egg incubator which contains poultry eggs at a time when not less than 40%, and preferably not less than 70%, of the eggs have hatched. The growth medium should be exposed for a time sufficient to collect a sample of bacteria including *E. coli* bacteria on the medium: preferably not less than five minutes, and most preferably for about fifteen minutes. The growth medium is then incubated and inspected as described above. The presence of colonies of E. coli which have taken up the dye indicates that the hatchlings of the eggs contained in the incubator from which the sample was collected will be afflicted with colisepticemia.

Dyes which can be used in practicing the present invention include Congo Red, Trypan Blue, Calcofluor, Tinopal and Brilliant Yellow. The structures of these dyes are set forth below.

Congo Red

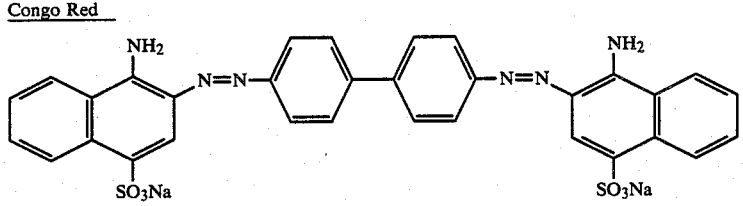

Trypan Blue

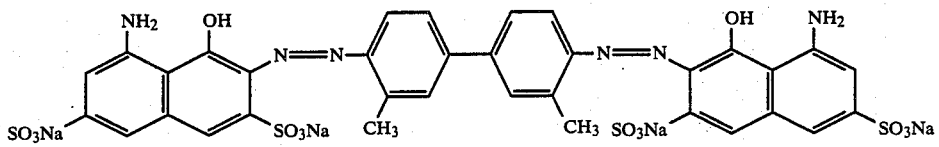

Calcofluor

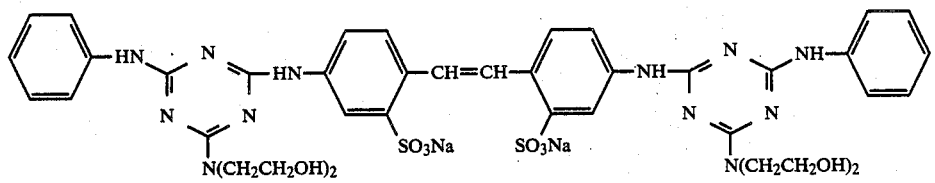

Tinopal

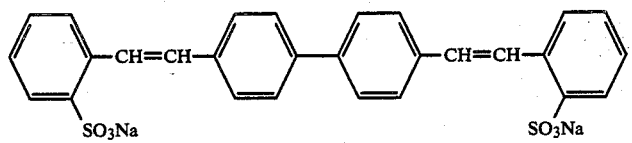

Brilliant Yellow

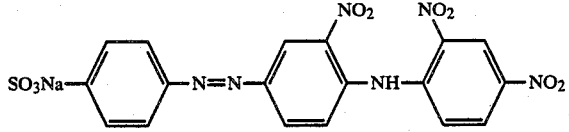

Examination of the structures of the dyes set forth above reveals that among the dyes which can be used in practicing the present invention are dyes generally represented by the formula "NaO$_3$S—X—Y=Y—Z," wherein X and Z are substituted or unsubstituted benzene rings, and Y is carbon or nitrogen. The pattern of substitutions on X and Z can be such that the "NaO$_3$S—X—" portion of the general formula above is repeated, or such that the "NaO$_3$S—X—Y=Y—" portion of the general formula is repeated. Examination of the specific examples set forth above will reveal that the term "substituted benzene ring" encompasses naphthalene ring systems. Of these dyes, Congo Red and Trypan Blue are preferred, and Congo Red is most preferred. The dye should be added to the growth medium in an amount effective to selectively stain invasive E. coli bacteria without staining either the harmless E. coli bacteria or other types of bacteria which may be included in the undifferentiated bacterial sample. For Congo Red dye, the growth medium should preferably contain from about 0.02% to about 0.07% of dye, more preferably from about 0.03% to about 0.06% of dye and most preferably 0.05% dye (Quantities herein expressed as percentages refer to the amount of the substance in grams added to 100 milliliters of solution during the preparation of the media, unless specified otherwise. Thus, 0.05% means 0.05 g/100 ml.).

As to the particular growth medium which should be used, good results have been obtained with both Lauria agar and Trypticase-soy agar (BBL, Cockeysville, Md.), with Lauria agar being most preferred. The growth medium should preferably include from about 0.1% to about 0.2% of bile salts, with 0.15% of bile salts most preferred. The pH of the growth medium should be adjusted to from 6.0 to 8.0, more preferably from about 7.0 to about 7.6, and should most preferably be 7.4.

We have found that the sensitivity of this procedure is improved if, following the collection of the undifferentiated bacterial sample, the bacteria are transferred to the growth medium before substantial growth of the bacteria in the sample has occurred. Although we do not wish to be bound to any particular theory by which this new observation can be explained, it appears that, when E. coli grow outside a living host (or in a deceased host), invasive E. coli multiply at a slower rate than noninvasive *E. coli*. As a result, the numbers of invasive *E. coli* in the sample decrease, and the probability of detecting them in any one culture of the sample decreases. Preferably, the bacteria are transferred to the growth medium within three hours after being taken from the host, more preferably within 15 minutes, and are most preferably transferred to the growth medium immediately after being taken from a host. If a lengthy delay is required, the bacteria should be stored in lyophylized form during the period between collection and inoculation of the growth medium. An appreciable decrease in the sensitivity of the procedure will occur if the undifferentiated bacterial sample is maintained, unlyophylized, on complex growth media and is passed consecutively on the media more than once without preferentially choosing the bacteria with the phenotype described herein (stained appearance resulting from uptake of dye). We have similarly found that if the undifferentiated bacterial sample is obtained from a host which has been dead for more than three hours, the sensitivity of the test is appreciably decreased (our observations were in chickens).

Invasive *E. coli* bacteria will better take up the dye if a two-step incubation procedure is used. In the first incubation step, the growth medium is incubated for a time not greater than 48 hours at a temperature sufficient to grow discrete colonies of *E. coli* (preferably from about 31° C. to about 43° C.). In the second incubation step, the bacteria should be incubated at a temperature of from about 20° C. to about 30° C. (most preferably 22° C.) for a time of from about three hours to not more than 96 hours. This second step promotes the selective uptake of the dye by invasive *E. coli* colonies. We have verified the superior results obtained with this procedure with both Congo Red dye and Trypan Blue dye. When Congo Red dye is used in this procedure, the colonies of invasive *E. coli* bacteria are found not only to take up the dye, but to have a wrinkled appearance.

The concept which is the present invention can be practiced in numerous ways. The following examples are provided to more fully illustrate the invention and are not to be considered restrictive thereof.

EXAMPLES 1–17

The following examples demonstrate that only those *E. coli* which take up Congo Red dye (CR-positive *E. coli*) will be found to have invaded the tissue of a living host.

Three hundred seventy *E. coli* cultures were isolated from broilers with and without colisepticemia. The isolates were from 30 different broiler farms (26 with colisepticemia and four healthy) located in central North Carolina. The isolates were obtained from infected pericardium, liver, air sacs, lung, heart, blood and joints of septicemic birds, from trachea and cloaca of clinically normal birds, and also from the poultry house environment (air, dust, waterers, feeders and litter). Primary isolations were made simultaneously on MacConkey agar and Congo Red growth medium, incubated aerobically at 37° C. for 18 hours. Final identification of *E. coli* was made with the AP1-20E (Analytab Products, Plainview, N.Y.). Enterobacteriaceae system. Cultures were maintained at 4° C. in Trypticase soy agar stabs (BBL, Cockeysville, Md.) "O" serotypes were identified at the *E. coli* Reference Center (Pennsylvania State University, Department of Veterinary Science, University Park, Pa).

The Congo Red growth medium (CR agar) used was Trypticase soy agar (BBL) supplemented with 0.03% of Congo Red dye (Sigma Chemical Co., St. Louis, Mo.) and 0.15% bile salts (Sigma Chemical Co.). The trypticase soy agar was comprised of pancreatic digest of casein (1.5%), papaic digest of soybean meal (0.5%), sodium chloride (0.5%), and agar (1.5%).

All of the 144 isolates recovered from internal tissues of birds with lesions of colisepticemia were CR-positive. Of 226 *E. coli* isolates from the poultry house environment, from the trachea and cloaca of healthy birds, and from the trachea and cloaca of septicemic birds, more than half were CR-negative, and the remainder were CR-positive. No CR-negative *E. coli* were isolated from internal tissues of septicemic birds.

Seventeen selected isolates of *E. coli* were studied in detail. Their serotypes and CR-binding ability are shown in Table 1.

TABLE 1

| Isolate[A] | Binds Congo Red[B] | O Serotype |
|---|---|---|
| 1-3THB[2] | No | NT[C] |
| 1-2THB[2] | No | NT |
| 3-5HHB[1] | Yes | O120 |
| 1-4AHB[1] | Yes | NT |
| 1-4LHB[1] | Yes | NT |
| 2-1CHB[2] | No | NT |
| 1-1HHB[1] | Yes | O2 |
| 1-1LHB[1] | Yes | O2 |
| 1-1AHB[1] | Yes | O2 |
| 1-1THB[2] | No | O2 |
| 2-4LHB[1] | Yes | NT |
| 19025-A[1] | Yes | O36:H12 |
| 19025-4-A[1] | Yes | O45 |
| 19025-1-L[1] | Yes | O45 |
| 19025-1-H[1] | Yes | O36:H12 |
| 19025-1-A[1] | Yes | O36:H12 |
| 18344-3-LW[1] | Yes | O2 |

[A]1 = Internal tissues; 2 = external tissues.
[B]Yes = Red colonies; No = white colonies.
[C]Not typable.

EXAMPLES 18–37

In these examples, the presence of colV plasmids in *E. coli* and the serotype of individual *E. coli* isolates were compared with the presence or absence of Congo Red uptake in those isolates. Both were found uncorrelated with Congo Red uptake.

We studied 20 *E. coli* avian strains obtained from Dr. H. W. Smith (Houghton Poultry Research Laboratories, Huntington, England). "O" serotypes were identified at the *E. coli* Reference Center (Pennsylvania State University, Department of Veterinary Science, University Park, Pa.). Congo Red uptake was determined according to the procedure set forth above. The results of these studies are set forth in Table 2.

TABLE 2

| Serotype | Strain Designation | Binds Congo Red |
|---|---|---|
| O2:K1 ColV+ | HWS-4593 | Yes |
| | HWS-4601 | Yes |
| | HWS-4627 | Yes |
| | HWS-4659 | No |
| | HWS-4603 | Yes |
| O2:K1 ColV− | HWS-4600 | No |
| | HWS-4613 | Yes |
| | HWS-4625 | Yes |
| | HWS-4656 | No |
| | HWS-4641 | Yes |
| O78:K80 ColV+ | HWS-4544 | Yes |
| | HWS-4619 | No |

TABLE 2-continued

| Serotype | Strain Designation | Binds Congo Red |
|---|---|---|
|  | HWS-4631 | Yes |
|  | HWS-4642 | Yes |
|  | HWS-4647 | No |
| Untyped ColV+ | HWS-4591 | No |
|  | HWS-4595 | Yes |
|  | HWS-4602 | Yes |
|  | HWS-4611 | No |
|  | HWS-4636 | Yes |

EXAMPLES 38-47

These examples confirm that CR-positive *E. coli* are invasive by demonstrating a strong correlation between CR-binding ability for a particular strain and lethality of the strain in chickens.

Mycoplasma-free broiler chicks were obtained from commercial sources (Perdue, Inc., Sanford, N.C.). They were kept in batteries under Biosafety Level 2 isolation procedures (U.S. Public Health Service, Centers for Disease Control) and were fed antibiotic-free commercial starter feed ration.

Cultures of *E. coli* were grown in Trypticase soy broth ($10^{10}$ colony-forming units [CFU] per ml) and TMM ($10^6$ CFU/ml). A 1-ml sample of cell suspension was used to inoculate four-week old broiler chicks via the caudal air sac. Chicks were observed for three days. Dead birds were examined for lesions of colisepticemia (fibrinous perihepatitis, pericarditis, airsacculitis and joint involvement). Surviving birds (sick and healthy) were sacrificed after the third day. Upon necropsy, all birds were cultured for *E. coli* on MacConkey and CR agar. *E. coli* strains that produced any or all of the above lesions were considered invasive (capable of producing septicemic disease).

Cultures prepared as described above were inoculated with 1.0 ml of a Trypticase soy suspension intraperitoneally into 18 to 20-g young adult white mice (Charles River). Pathogenicity for mice was based on death of the mice. *E. coli* was reisolated from liver and spleen on MacConkey and CR agar.

Results of pathogenicity studies with 10 *E. coli* isolates and strains are shown in Table 3. A strong correlation between the CR-binding ability and lethality for chickens and mice was found.

TABLE 3

| Strain | Binds Congo Red[A] | Lethal for Chickens | Lethal for Mice |
|---|---|---|---|
| 18344-3-LR | Yes | 8/8 | 8/8 |
| 18344-3LR[B] | No | 0/8 | 0/7 |
| 1476 (K-12) | No | 0/13 | 0/13 |
| 19025-4-AR | Yes | 9/10 | 10/10 |
| 19025-4-AR[B] | No | 0/11 | 0/11 |
| 3-5HHB-R | Yes | 8/10 | ND[C] |
| 3-5HHB-W[B] | No | 0/12 | ND |
| HWS4603 | Yes | 29/30 | ND |
| HWS4591 | No | 0/5 | ND |
| HWS4600 | No | 0/5 | ND |

[A]Yes = Red colonies; no = white colonies.
[B]Spontaneous mutuant.
[C]Not done

EXAMPLES 48-49

These examples demonstrate how outbreaks of colisepticemia in poultry can be predicted by taking undifferentiated bacterial samples from the hatchery and breeder flocks.

Bacteriological samples were taken by direct swabbing from the environment of poultry houses (litter, waterer, feeder, dust). Direct swabbing was performed by sampling the above regions with culture swabs (Precision culture C.A.T.S. Precision Dynamics Corp., Burbank, Calif.). Bacteria from the swabs were isolated onto CR agar and MacConkey agar for preliminary identification. Final identifications were made with API-20E strips. Air was sampled to enumerate and identify *E. coli* in the atmosphere of the poultry houses. Air samples were cultured onto CR agar and MacConkey agar using a Model 200 Mattson Garvin air sampler (Mattson-Garvin, Maitland, Fla.). Time of sampling was 15 minutes to allow 15 cubic feet of air to be measured. Cloacal swabs were taken from a random sampling of hens and toms in the breeder flocks. Air samples were taken from the hatchery by placing uncovered plates of growth media containing Congo Red dye on the top rack in the incubators for a period of 15 minutes at the point in the incubation cycle when approximately 80% of the eggs had hatched.

Repeated attempts to isolate CR-positive *E. coli* from poultry houses using an air-sampling device (slit sampler) consistently yielded only gram-positive bacteria (mostly Micrococcus sp.) and eukaryotic microorganisms (Penicillium sp.). CR-positive *E. coli* were not isolated suggesting that the number of CR-positive *E. coli* in the air was below detectable numbers, even at times of high incidence of *E. coli* related air-sac disease. A survey of the hatchery and breeder flocks showed that CR-positive *E. coli* were present in both places and that the presence of CR-positive *E. coli* in the cloaca of breeder hens and in the hatchery at the time of hatching predicted the occurrence of severe *E. coli* septicemia and airsacculitis outbreaks in commercial broiler chicks.

EXAMPLES 50-61

These examples demonstrate the use of Trypan Blue in practicing the present invention, and the variety of different growth media on which the present invention can be practiced.

The growth media set forth in Table 4 were prepared with both Congo Red and Trypan Blue dye.

TABLE 4

| Brain Heart Infusion Agar (per liter) | |
|---|---|
| Brain Heart, infusion from solids | 6.0 grams |
| Peptic digest of animal tissue | 6.0 g |
| Sodium Chloride | 5.0 g |
| Dextrose | 3.0 g |
| Pancreatic digest of gelatin | 14.5 g |
| Disodium Phosphate | 2.5 g |
| Congo red/Trypan blue | 0.4 g |
| Agar | 15.0 g |
| Bile Salts | 1.5 g |
| Muller-Hinton Agar (per liter) | |
| Beef extract | 2.0 g |
| Acid hydrolysate of caselin | 17.5 g |
| Starch | 1.5 g |
| Congo red/Trypan blue | 0.4 g |
| Agar | 15.0 g |
| Bile Salts | 1.5 |
| Trypticase Soy Agar (per liter) | |
| Pancreatic digest of casein | 15.0 g |
| Papaic digest of soybean meal | 5.0 g |
| Sodium chloride | 5.0 g |
| Congo red/Trypan blue | 0.4 g |
| Agar | 15.0 g |
| Bile Salts | 1.5 g |
| Nutrient Agar (per liter) | |

TABLE 4-continued

| | |
|---|---|
| Bacto-beef extract | 3.0 g |
| Bacto-peptone | 5.0 g |
| Congo red/Trypan blue | 0.4 g |
| Agar | 15.0 g |
| Veal Infusion Agar (per liter) | |
| Veal, infusion from solids | 10.0 g |
| Polypeptone peptone | 10.0 g |
| Sodium chloride | 5.0 g |
| Congo red/Trypan blue | 0.4 g |
| Agar | 15.0 g |
| Bile salts | 1.5 g |
| Lauria Agar (per liter) | |
| Bactone tryptone | 10.0 g |
| Yeast extract | 5.0 g |
| Sodium Chloride | 10.0 g |
| Tris (pH 7.3) 0.5 M stock solution | 10.0 ml |
| Congo red/Trypan blue | 0.5 g |
| Agar | 15.0 g |
| Bile Salts | 1.5 g |

With all growth media both Trypan Blue and Congo Red were selectively taken up by invasive *E. coli* bacteria, but the results obtained with Trypan Blue were slightly more difficult to interpret because of background contrast. The most preferred growth media was Lauria agar. With Lauria agar containing 0.05% Congo Red dye, the first incubation step is most preferably carried out at 37° C. for a time of from 18 to 24 hours. After this step alone differentiation of invasive and noninvasive bacteria has been and will be seen, but the results are more difficult to interpret. A second incubation step is therefore preferably carried out at about 22° C. (room temperature) for at least three hours, and most preferably for eight hours.

EXAMPLE 62

It is generally recognized that the drying of plates of growth media to remove excess water is a preferred laboratory practice. Nevertheless, for various reasons, this practice is not always followed. We have observed, however, that the wetter the growth media is (such as in freshly poured plates), the worse the results which are obtained with the present invention will be. Stated in positive terms, the drier the plate of growth media, the better and faster the invasive *E. coli* bacteria will take up the dye. The growth media should therefore be dried at room temperature for not less than 12 hours, and preferably for 24 to 48 hours (or receive equivalent treatment in a drying room). Some growth media will become completely dried and unuseable in three to five days, which imposes an upper limit on the drying time. The optimum drying time will vary from lab to lab according to temperature, humidity, air activity and the availability of drying rooms, as those skilled in the art will readily appreciate.

The foregoing examples are illustrative of the present invention rather than restrictive. Those modifications of the invention which come within the meaning and range of equivalents of the claims are to be included therein.

That which is claimed:

1. A method for distinguishing *Escherichia coli* (*E. coli*) bacteria which can invade the tissue of a host animal from those that cannot, comprising:
    (a) collecting an undifferentiated bacterial sample containing *E. coli* from a host animal; and then before substantial growth of the bacteria in said sample has occurred
    (b) contacting bacteria contained in said sample to a growth medium containing a dye which is selectively taken up by invasive *E. coli* bacteria so that the growth medium is inoculated with *E. coli* bacteria;
    (c) incubating said growth medium for a time sufficient to grow colonies of said *E. coli* bacteria; and
    (d) detecting the presence or absence of *E. coli* colonies which have taken up said dye, the presence of which colonies indicate the presence of invasive *E. coli* in said host.

2. A method for distinguishing *Escherichia coli* bacteria as claimed in claim 1, wherein said growth medium contains a dye selected from the group consisting of Congo Red, Trypan Blue, Calcofluor, Tinopal and Brilliant Yellow.

3. A method for distinguishing *Escherichia coli* bacteria as claimed in claim 1, wherein said growth medium contains Congo Red dye in an amount effective to selectively stain invasive *E. coli* bacteria.

4. A method for distinguishing *Escherichia coli* bacteria as claimed in claim 1, wherein said growth medium contains from about 0.02% to about 0.07% of Congo Red dye.

5. A method of distinguishing *Escherichia coli* bacteria as claimed in claim 4, wherein said growth medium further comprises from about 0.1 to about 0.2 percent of bile salts.

6. A method of distinguishing *Escherichia coli* bacteria as claimed in claim 5, wherein said growth medium is Lauria agar.

7. A method for distinguishing *Escherichia coli* (*E. coli*) bacteria which can invade the tissue of a host animal from those that cannot, comprising:
    (a) collecting an undifferentiated bacterial sample containing *E. coli* from the host animal, and then before substantial growth of the bacteria in said sample has occurred
    (b) contacting bacteria contained in said sample to a growth medium containing a dye which is selectively taken up by invasive *E. coli* bacteria so that the growth medium is inoculated with *E. coli* bacteria;
    (c) incubating said growth medium in a first incubation step for a time of not more than 48 hours at a temperature sufficient to grow colonies of *E. coli*; followed by
    (d) incubating said growth medium in a second incubation step at a temperature of from 20° C. to 30° C. for a time of from about 3 hours to not more than about 96 hours; and
    (e) detecting the presence or absence of *E. coli* colonies which have taken up said dye, the presence of which colonies indicate the presence of invasive *E. coli* bacteria in said host.

8. A method for distinguishing *Escherichia coli* bacteria as claimed in claim 7, wherein the dye contained in said growth medium is selected from the group consisting of Congo Red, Trypan Blue, Calcofluor, Tinopal and Brilliant Yellow.

9. A method for distinguishing *Escherichia coli* bacteria as claimed in claim 7, wherein said growth medium contains Congo Red dye in an amount effective to selectively stain invasive *E. coli* bacteria.

10. A method of distinguishing *Escherichia coli* bacteria as claimed in claim 7, wherein said first incubation step is carried out at a temperature of from about 31° C. to about 43° C.

11. A method for distinguishing *Escherichia coli* bacteria as claimed in claim 7, wherein said growth medium contains from about 0.02% to about 0.07% of Congo Red dye.

12. A method of distinguishing *Escherichia coli* bacteria as claimed in claim 11, wherein said growth medium further comprises from about 0.1% to about 0.2% of bile salts.

13. A method of distinguishing *Escherichia coli* bacteria as claimed in claim 11, wherein said growth medium is Lauria agar.

14. A method for predicting the occurrence of colisepticemia in the offspring of a poultry breeder flock, comprising:
  (a) collecting undifferentiated bacterial samples containing *Escherichia coli* (*E. coli*) from the cloacas of selected birds in said breeder flock; and then before substantial growth of the bacteria in said samples has occurred
  (b) contacting bacteria contained in said samples to a growth medium which includes a dye which is selectively taken up by *E. coli* bacteria so that the growth medium is inoculated with *E. coli* bacteria;
  (c) incubating said growth medium for a time sufficient to grow colonies of said *E. coli*; and
  (d) detecting the presence or absence of colonies of *E. coli* which have taken up said dye, the presence of which colonies indicate that the offspring of said breeder flock will be afflicted with colisepticemia.

15. A method for predicting the occurrence of colisepticemia in the offspring of a poultry breeder flock as claimed in claim 14, wherein the dye contained in said growth medium is selected from the group consisting of Congo Red, Trypan Blue, Calcofluor, Tinopal and Brilliant Yellow.

16. A method for predicting the occurrence of colisepticemia in the offspring of a poultry breeder flock as claimed in claim 14, wherein said growth medium contains Congo Red dye in an amount effective to selectively stain invasive *E. coli* bacteria.

17. A method for predicting the occurrence of colisepticemia in the offspring of a poultry breeder flock as claimed in claim 14, wherein said growth medium contains from 0.02% to 0.07% of Congo Red dye.

18. A method for predicting the occurrence of colisepticemia in the offspring of a poultry breeder flock as claimed in claim 17, wherein said growth medium further comprises from about 0.1% to about 0.2% of bile salts.

19. A method for predicting the occurrence of colisepticemia in the offspring of a poultry breeder flock as claimed in claim 18, wherein said growth medium is Lauria agar.

20. A method for predicting the occurrence of colisepticemia in the offspring of a poultry breeder flock, comprising:
  (a) collecting an undifferentiated bacterial sample containing *Escherichia coli* (*E. coli*) from the cloacas of selected birds in said breeder flock, and then before substantial growth of the bacteria in said sample has occurred
  (b) contacting the bacteria contained in said samples to a growth medium which includes an amount of Congo Red dye effective to selectively stain invasive *E. coli* bacteria so that the growth medium is inoculated with *E. coli* bacteria;
  (c) incubating said growth medium for a time not greater than 48 hours at a temperature sufficient to grow colonies of *E. coli*; followed by
  (d) incubating said growth medium in a second incubation step at a temperature of from 20° C. to 30° C. for a time of from about 3 hours to not more than about 96 hours to promote the selective uptake of the dye by said *E. coli* colonies; and
  (e) detecting the presence or absence of red, wrinkled *E. coli* colonies, the presence of which colonies indicate that the offspring of said breeder flock will be afflicted with colisepticemia.

21. A method for predicting the occurrence of colisepticemia in the offspring of a poultry breeder flock as claimed in claim 20, wherein said growth medium contains from 0.02% to 0.07% of Congo Red dye.

22. A method for predicting the occurrence of colisepticemia in the offspring of a poultry breeder flock as claimed in claim 21, wherein said growth medium is Lauria agar.

23. A method for predicting the occurrence of colisepticemia in poultry, comprising:
  (a) exposing a growth medium which includes a dye which is selectively taken up by invasive *Escherichia coli* (*E. coli*) bacteria to the atmosphere within a poultry egg incubator containing poultry eggs at a time when not less than 40% of said eggs have hatched, for a time sufficient to collect a sample of bacteria including *E. coli* on the growth medium;
  (b) incubating said growth medium for a time sufficient to grow colonies of *E. coli*; and
  (c) detecting the presence or absence of colonies of *E. coli* which have taken up said dye, the presence of which colonies indicate that the hatchlings of said eggs will be afflicted with colisepticemia.

24. A method for predicting the occurrence of colisepticemia in the offspring of a poultry breeder flock as claimed in claim 23, wherein the dye contained in said growth medium is selected from the group consisting of Congo Red, Trypan Blue, Calcofluor, Tinopal and Brilliant Yellow.

25. A method for predicting the occurrence of colisepticemia in the offspring of a poultry breeder flock as claimed in claim 23, wherein said growth medium includes Congo Red dye in an amount effective to selectively stain invasive *E. coli* bacteria.

26. A method for predicting the occurrence of colisepticemia in the offspring of a poultry breeder flock as claimed in claim 23, wherein said growth medium is exposed to the atmosphere within the poultry egg incubator at a time when not less than 70% of said eggs have hatched.

27. A method for predicting the occurrence of colisepticemia in the offspring of a poultry breeder flock as claimed in claim 23, wherein said growth medium includes from about 0.02% to about 0.07% of Congo Red dye.

28. A method for predicting the occurrence of colisepticemia in the offspring of poultry breeder flock as claimed in claim 27, wherein said growth medium further comprises from about 0.1% to about 0.2% of bile salts.

29. A method for predicting the occurrence of colisepticemia in the offspring of a poultry breeder flock as claimed in claim 28, wherein said growth medium is Lauria agar.

30. A method for predicting the occurrence of colisepticemia in poultry, comprising:

(a) exposing a growth medium which includes an amount of Congo Red dye effective to selectively stain invasive *Escherichia coli* (*E. coli*) bacteria to the atmosphere within a poultry egg incubator containing poultry eggs at a time when not less than 40% of said eggs have hatched, for a time sufficient to collect a sample of bacteria including *E. coli* on the growth medium;

(b) incubating said growth medium for a time not greater than 48 hours at a temperature sufficient to grow colonies of *E. coli*, followed by (c) incubating said growth medium in a second incubation step at a temperature of from 20° C. to 30° C. for a time of from about 3 hours to not more than about 96 hours to promote the selective uptake of the dye by invasive *E. coli* colonies; and (d) detecting the presence or absence of red, wrinkled *E. coli* colonies, the presence of which colonies indicate that the hatchlings of said eggs will be afflicted with colisepticemia.

31. A method for predicting the occurrence of colisepticemia in the offspring of a poultry breeder flock as claimed in claim 30, wherein said growth medium is exposed to the atmosphere within the poultry egg incubator at a time when not less than 70% of said eggs have hatched.

32. A method for predicting the occurrence of colisepticemia in the offspring of a poultry breeder flock as claimed in claim 30, wherein said growth medium contains from 0.02% to 0.07% of Congo Red dye.

33. A method for predicting the occurrence of colisepticemia in the offspring of a poultry breeder flock as claimed in claim 32, wherein said growth medium further comprises from about 0.1% to about 0.2% of bile salts.

34. A method for predicting the occurrence of colisepticemia in the offspring of a poultry breeder flock as claimed in claim 33, wherein said growth medium is Lauria agar.

* * * * *